United States Patent [19]

Marlett

[11] Patent Number: 4,925,963
[45] Date of Patent: May 15, 1990

[54] PROCESS FOR REDUCTION OF ORGANOSILICON HALIDES

[75] Inventor: Everett M. Marlett, Baton Rouge, La.

[73] Assignee: Ethyl Corporation, Richmond, Va.

[21] Appl. No.: 420,757

[22] Filed: Oct. 12, 1989

[51] Int. Cl.$^5$ .............................................. C07F 7/08
[52] U.S. Cl. .................................................... 556/474
[58] Field of Search ........................................ 556/674

[56] References Cited

U.S. PATENT DOCUMENTS

| | | | |
|---|---|---|---|
| 2,567,972 | 9/1951 | Schesinger et al. | 556/474 X |
| 2,576,311 | 11/1951 | Schlesinger et al. | 556/474 X |
| 2,857,414 | 10/1958 | Schmidt et al. | 260/448 |
| 3,398,171 | 8/1968 | Giraitis et al. | 260/448 |
| 3,499,020 | 3/1970 | Robinson | 556/474 |
| 3,926,833 | 12/1975 | Hoffman et al. | 252/188 |
| 4,006,095 | 2/1977 | Hoffman et al. | 252/188 |
| 4,367,343 | 1/1983 | Tamborski et al. | 556/478 |
| 4,474,743 | 10/1984 | Marlett | 423/347 |
| 4,542,005 | 9/1985 | Tetsuya et al. | 556/474 X |
| 4,595,777 | 6/1986 | Bakshi et al. | 556/478 |
| 4,665,207 | 5/1987 | Marlett | 556/176 |
| 4,683,321 | 7/1987 | Nelson | 556/478 |
| 4,711,965 | 12/1987 | Nelson | 556/478 |
| 4,711,966 | 12/1987 | Nelson | 556/478 |
| 3,6277,803 | 12/1971 | Michael | 556/474 |

FOREIGN PATENT DOCUMENTS 0825987 12/1959 United Kingdom ................ 556/474

OTHER PUBLICATIONS

Wibert et al., "Hydrides of the Elements of Main Groups I–IV", Elsevier Publishing Co., Amsterdam (1971), pp. 490 and 496.

Reduction of Silicon Halides, Chem. Abstracts 22009v, vol. 67, 1967, Silicon Halides Reduced by NaAlH$_4$ or NA$_3$AlH$_6$ in the presence of a polyether.

Tamborski et al., *Ind. Eng. Chem. Prod. Res. Dev.* 22, 172–178 1893.

Van Dyke, in "The Bonds to Halogens and Halogenoids", Edited by A. G. MacDiarmid, Marcel Dekker, Inc., New York (1972) Part I, pp. 234–240.

*Primary Examiner*—Paul F. Shaver

[57] ABSTRACT

A process for the reduction of an organosilicon halide to an organosilicon hydride using an amine alane hence avoiding the problem of dismutation of the hydrocarbyl group as well as avoiding cleavage of the silicon-carbon bonds associated with other methods for reduction of organosilicon halides.

19 Claims, No Drawings

PROCESS FOR REDUCTION OF ORGANOSILICON HALIDES

TECHNICAL FIELD

This invention provides a method for selective reduction of an organosilicon halide to an organosilicon hydride while avoiding the problem of dismutation of hydrocarbyl groups as well as avoiding the cleavage of the silicon carbon bonds.

BACKGROUND

It is known that $LiAlH_4$, $AlH_3$, and $NaAlH_4$ are effective reducing agents for a number of organic compounds. See for example U.S. Pat. Nos. 4,006,095, and 3,926,833. However if the organic compound is a halogenated organosilicon compound, by-product $AlCl_3$ thus produced can catalyze dismutation (Si-C cleavage) of the hydrides that are formed. Additionally, $AlCl_3$ can induce polymerization or isomerization when reducing alkenylchlorosilanes. Consequently, the reaction mixture may have to be hydrolyzed, or the hydride extracted from the reaction solution with petroleum ether before fractionation in order to obtain the desired product.

Organosilanes are useful in the production of tetraalkysilanes which in turn are suitable for use in formulating hydraulic fluids and lubricants which are stable at high temperatures. One means of converting organosilanes to tetraalkylsilanes suitable for use in the formulation of hydraulic fluids and lubricants stable at high temperatures is described in U.S. Pat. No. 4,595,777, the disclosure of which is incorporated herein by reference. Organosilanes are also useful in the formation of polymethylhydrosiloxanes which in turn are useful in the textile industry to waterproof and improve the wear resistance of fabrics.

The reaction of organohalosilanes with metal hydrides such as $LiAlH_4$, and $NaAlH_4$, is usually conducted in an anhydrous solvent such as diethyl ether, tetrahydrofuran, diglyme, or dioxane because of the low solubility of the metal hydride in liquid hydrocarbon media. The extent and efficiency of the reaction is dependant on intimate contact of the reactants, hence solubility of the reducing agent is an important consideration.

Of the reducing agents, $AlH_3$ is known to be a selective hydrogenating and reducing agent for various organic reactions. One method of producing $AlH_3$ is a two step procedure, starting with LiH, wherein the latter is initially reacted with $AlCl_3$ in the presence of certain ethers, notably, diethylether, to produce lithium tetrahydridoaluminate or lithium aluminum hydride ($LiAlH_4$), and the latter is then reacted with $AlCl_3$ in the presence of ether, usually diethylether. Unfortunately, solutions of $AlH_3$ are quite unstable in ethers. See for example, U.S. Pat. No. 4,006,095.

Alkali metal hydrides, such as NaH or LiH have also been used to reduce organosilicon halides to the hydrides, however high temperatures are usually required (e.g., 200°-300° C.) and the hydrides are often produced in low yields. In the case of alkali metal hydrides, polar solvents such as hexamethylphosphoric triamide or tetramethylurea are required.

Not all chlorosilanes can be reduced successfully using NaH in ether solvents. Dimethyldichlorosilane is not reduced by NaH even on prolonged refluxing in dioxane. See Charles H. Van Dyke "The Bond to Halogens and Halogenoids," Marcel Dekker, Inc. N.Y., 1972, pp. 234–240. Nevertheless, the use of alkali metal hydrides does avoid the formation of $AlCl_3$ which has the disadvantages noted previously.

THE INVENTION

This invention involves the novel discovery that an organosilicon halide can be reduced to an organosilicon hydride with an amine alane, even at room temperature. By using an amine alane, it has been found, surprisingly, that redistribution (dismutation) of hydrocarbyl groups on hydrocarbylsilicon hydrides can be avoided. In addition, products of this process can more readily be separated from the reactants by distillation techniques. Separation of the products by distillation is generally more efficient and easier than separation by extraction techniques which usually require additional processing steps in order to separate the solvent from the product. Other advantages of this process will become evident from the ensuing description.

In accordance with this invention, reaction between an organosilicon halide and an amine alane forms an organosilicon hydride and co-product aluminum halide. The aluminum halide thus formed may be complexed or weakly complexed with the amine, the strength of the complex thus varying depending on the reactants used. Regardless of the actual mechanism involved in the process of this invention, it has been observed that the presence of the amine retards the cleavage of the silicon-carbon bonds normally experienced when aluminum halide in the absence of an amine is present, and dismutation of the alkyl groups is avoided.

The organosilicon halides which may be used in the process of this invention may generally be represented by the formula $$(R)_p SiX_{4-p} \qquad (I)$$

where each R is independently, a hydrocarbyl group such as alkyl, cycloalkyl, aryl, aralkyl, alkenyl, alkynyl, or a substituted hydrocarbyl group such as haloalkyl, halocycloalkyl, haloaryl, haloaralkyl, haloalkenyl, haloalkynyl, and the like; p is an integer from 1 to 3; and X is chlorine, bromine, fluorine, or iodine. In addition, one or more hydrocarbyl groups may contain inert substituents such as alkoxy, cycloalkoxy, aryloxy, and the like. Each such hydrocarbyl group may contain up to about 24 or more carbon atoms but preferably contains up to about 18 carbon atoms, and most preferably, about 12 carbon atoms. The halogen substituent on the hydrocarbyl group may be the same or may differ from the halogen bonded to the silicon molecule. In addition, the hydrocarbyl groups bonded to the silicon may differ from each other, but preferably are identical to each other.

Typical organosilicon halides that may be used in the process of this reaction include the following:
dimethyldichlorosilane,
trimethylbromosilane,
trimethylchlorosilane
trimethyliodosilane,
triethylchlorosilane
trihexylchlorosilane,
ethyltrichlorosilane
methyltrichlorosilane
methylpropyldichlorosilane
ethylmethyldichlorosilane, n-propyltrichlorosilane
3-chloropropyltrichlorosilane
t-butyldimethylchlorosilane
n-butyltrichlorosilane
n-hexylmethyldichlorosilane
hexyltrichlorosilane
octyltrichlorosilane,
n-decyltrichlorosilane,
n-dodecyltrichlorosilane,
octadecyltrichlorosilane,
n-docosylmethyldichlorosilane
tetradecyltrichlorosilane
cyclohexyldimethylchlorosilane
2-(bicycloheptyl)dimethylchlorosilane
(cyclohexylmethyl)trichlorosilane
vinyltrichlorosilane
allyltrichlorosilane
allylmethyldichlorosilane,
methylvinyldichlorosilane,
6-hex-1-enyldimethylchlorosilane
2-propynyltrifluorosilane,
2-pentynyltrichlorosilane,
benzyldimethylchlorosilane,
t-butyldiphenylchlorosilane,
(p-t-butylphenethyl)dimethylchlorosilane
phenyltrichlorosilane
methylphenyldichlorosilane
dimethylphenylchlorosilane
diphenyldichlorosilane
diphenyldifluorosilane,
triphenylchlorosilane
2-phenylethyltrichlorosilane,
p-tolyltrichlorosilane
8-bromooctyltrichlorosilane
α-bromovinyltrichlorosilane,
(chloromethyl)(dimethyl)chlorosilane,
p-(chloromethyl)phenyltrichlorosilane
3,3,3-trifluoropropyltrichlorosilane,
p-(bromophenyl)trichlorosilane
pentafluorophenyldimethylchlorosilane
chlorinated diphenyldichlorosilane
t-butylpentafluorophenylmethylchlorosilane,
3-acetoxypropyltrichlorosilane
(4-methoxyphenyl)dimethylchlorosilane,
(2,4,6-tri-t-butylphenoxy)dimethylchlorosilane, and the like.

This process may also be used in the reduction of bisorganosilicon halide compounds of the general formula

$X_{3-p}R'_pSi—(R)—SiR'_pX_{3-p}$ (II)

In Formula (II), the R radical is an alkyl, cycloalkyl, or aryl group with about 2 to about 24 carbon atoms but more preferably contains about 18 carbon atoms, and most preferably, about 6 carbon atoms; R' a hydrocarbyl group such as alkyl, cycloalkyl, aryl, or aralkyl with about 1 to about 24 carbon atoms, but more preferably contains about 18 carbon atoms, and most preferably, about 4 carbon atoms; p is an integer from 0 to 2; and X is chlorine, bromine, fluorine, or iodine.

Typical bis-organosilicon halides that may be used in the process of this reaction include the following:
1,2-bis(chlorodimethylsilyl)ethane,
1,6-bis(chlorodimethylsilyl)hexane,
1,8-bis(chlorodimethylsilyl)octane,
1,4-bis[2-(chlorodimethylsilyl)ethyl]benzene, and the like.

The process of this invention is particularly important due to the high yields obtained when an amine alane is used as the co-reactant. Any tertiary amine alane can be used that is co-reactive with an organosilicon halide. The tertiary amine portion of the complex may thus be aromatic, heterocyclic, aliphatic or cycloaliphatic. Preferred are the trialkylamine alane complexes such as trimethylamine alane, tripropylamine alane, tributylamine alane, and like straight and branched chain trialkylamine alane complexes wherein each alkyl group which may contain up to about 12 carbon atoms but which preferably contains from 1 to 6 carbon atoms. However, compounds in which one to two equivalents of alane is/are complexed with a tertiary diamine such as the triethylenediamine and N,N,N',N'-tetramethylethylenediamine complexes may also be employed.

Other examples of tertiary amine alanes that may be used in the process include tricyclohexylamine alane, N,N-dimethylethylamine alane, N,N-diethylmethylamine alane, N-methylmorpholine alane, quinuclidine alane, and the like. Preparation of the amine alanes found useful in this process can be found in Marlett, U.S. Pat. No. 4,665,207, issued May 12, 1987 incorporated herein by reference.

Of the amine alanes found useful in the process of this invention, the triloweralkyl amine alanes are the particularly preferred. By triloweralkyl is meant that the alkyl groups each contain 6 carbon atoms or less. Of the triloweralkyl amine alanes which may be used as co-reactants, trimethylamine alane and triethylamine alane are the most preferred.

It has been discovered, that the process of this invention proceeds rapidly at ambient temperatures. However, the reaction also proceeds at temperatures as low as −20° C. and as high as 150° C. The upper temperature limit is controlled by the stability of the amine alane at the higher temperature. In a preferred embodiment of the invention, the process is initiated at about room temperature (e.g., about 25° C.) and thereby proceeds to completion. As noted previously, high temperatures (e.g., 200°–300° C.) are required to initiate and conduct the reduction of organosilicon halides to the hydrides when alkali metal hydrides are used as the reducing agents. Hence, the ability to obtain good yields when initiating the reaction at room temperature, makes the process of this invention particularly advantageous.

The process can also be carried out at subatmospheric as well as superatmospheric pressures. However, it is more desirable to conduct the reaction in the range of about 1 to 2 atmospheres in order to minimize the cost of the reaction vessels.

It is not required that the reaction be carried out in the liquid phase, as vapor phase reactions are also feasible. In conducting vapor phase reactions, efficient contact of the reactants should be ensured. It is more preferable, however, to conduct the reaction in the liquid phase and most preferably in the presence of a suitable solvent.

A broad variety of hydrocarbons may be used as the medium for conducting the reaction, however as mentioned previously, a solvent is not required. If the reaction is conducted in the liquid phase with a solvent for reactants, it is preferable to use a solvent having a boiling point sufficiently different than the organosilane product such that separation of the solvent from the product by distillation can be accomplished more readily. When selecting a suitable solvent, the boiling point of the solvent should be at least 5° C. higher or lower than the organosilicon hydride. Preferably, the difference in boiling point between the solvent and the organosilicon hydride should be in the range of about 5° to about 25° C., and most preferably in the range of about 7° to about 20° C. However, a solvent with smaller than 5° C. or greater than 25° C. difference in boiling point as compared to the organosilane product, may also be used.

Solvents suitable in the process of this reaction include paraffinic hydrocarbons, cycloparaffinic hydrocarbons, aromatic hydrocarbons, dialkyl ethers, cyclic ethers, tertiary amines, tertiary (alkoxyalkyl) amines, and like materials (including mixtures of two or more such materials) which are in the liquid state under the reaction conditions selected for use. Of the liquid aromatic hydrocarbon solvents, the more preferred are benzene, toluene, o-xylene, m-xylene, p-xylene, ethylbenzene, trimethylbenzenes, 1,2-diethylbenzene, 1,3-diethylbenzene, 1,4-diethylbenzene, 3,5-diethyltoluene, n-butylbenzene, 3-propyltoluene, 4-propyltoluene, 1,2,3,4-tetrahydronaphthalene, 1,2,3,4-tetramethylbenzene, 1,2,3,5-tetramethylbenzene, and the like, including mixtures of two or more such materials. Mixtures of two or more different types of solvents, such as a mixture of paraffinic and aromatic hydrocarbons, a mixture of one or more hydrocarbons with one or more tertiary amines, etc., may also be used.

While the reaction proceeds rapidly when a stoichiometric amount of reactants is used, it is more desirable to have a molar excess of the amine alane present. The molar excess of amine alane may range from 0 to about 25%. In the most preferred embodiment of the process, the amine alane is present in a molar excess of about 2 to about 10%.

The reaction of the organosilicon halide and the amine alane proceeds rapidly by either adding the organosilicon halide to the amine alane or the amine alane to the organosilicon halide, or by adding the reactants to a vessel essentially simultaneously. In a preferred embodiment, the organosilicon halide is added to the amine alane which is formed in situ in a solvent compatible with this process and hence separation of the amine alane from the solvent prior to reaction with the organosilicon halide is not necessary.

The means for conducting the reaction is not critical to the process of this invention. The process of this invention can be carried out either in a batch; continuous, or semi-continuous reaction system. However, reaction times may vary widely, ranging from a few minutes up to an hour or more depending on the temperature, the amount of reactants present, agitation of the reactants, the means for conducting the reaction, etc.

Having described the basic concepts of this invention, reference will not be made to the following specific examples which are illustrative but not limitative of its practice.

EXAMPLE 1

Reduction of n-hexylmethyldichlorosilane

The amine alane used in this example was prepared by adding about 1 gram of $AlCl_3$ (99%), 20 grams of toluene, and about 3 grams of triethylamine (99%) to a 50-mL round-bottomed flask. When the $AlCl_3$ was all dissolved and cool, about 1.5 grams of $NaAlH_4$ (97%) was added and agitated 4 hours at room temperature. The resultant slurry was then filtered to give about 22 grams of a water-white solution of the triethylamine alane.

Nine grams of n-hexylmethyldichlorosilane was added to the 22 grams of triethylamine alane solution, and the mixture was stirred at room temperature (about 25° C.) for 2 hours then allowed to stand overnight. The reaction mixture was then placed into a 100-mL round bottomed flask and a short path distillation head was attached along with a receiver and nitrogen bubbler. The flask was immersed in a 150° C. oil bath and the mixture distilled at atmospheric pressure to remove the toluene and product from the aluminum chloride-amine complexes. After 30 minutes, a first cut (cut 1) of about 20 grams of distillate was recovered, while maintaining the overhead temperature in the range of 108 to 118° C. Next, the material remaining in the flask was vacuum distilled (10 mm Hg) in a 100° C. oil bath for 15 minutes and a second cut (cut 2) of 3 grams of distillate was recovered. Nuclear magnetic resonance (NMR) analysis of the distillates yielded the following results: cut 1 was 17 wt % n-hexylmethylsilane, 79 wt % toluene, and 4 wt % triethylamine; cut 2 was 53 wt % n-hexylmethylsilane, 34 wt % toluene, and 13 wt % triethylamine. Hence about 87% of the n-hexylmethyldichlorosilane was converted to the n-hexylmethylsilane (n-Hex-MeSiH$_2$). An aluminum chloridetriethylamine complex was recovered in the distillation residue.

EXAMPLE 2

Reduction of diphenyldifluorosilane

The triethylamine alane was prepared in the same manner as Example 1 above. Ten grams of diphenyldifluorosilane was added all at once to a 50-mL round bottomed flask containing about 23 grams of the triethylamine alane solution. A white precipitate formed quickly giving a thick white slurry. The slurry was magnetically stirred for 3 hours, and filtered over a coarse glass frit to recover about 24 grams of filtrate and about 9 grams of wet filter cake. The wet filter cake was washed with two 5-mL portions of dry toluene, then the cake was dried under a partial vacuum (1 mm Hg; 80° C.; 2 hours). The resulting dry filter cake weighed about 2 grams.

About 22 grams of the filtrate were placed in a 50-mL round bottomed flask fitted with a short path length distilling head. The condenser was cooled with ice water and the receiver was cooled with dry ice. The flask was heated at atmospheric pressure for 20 minutes with an oil bath, such that the flask contents were heated to the range of 140° to 160° C. A first cut of about 14 grams of distillate was recovered, while maintaining the overhead temperature in the range of 98° to 112° C. When the temperature dropped to 70° C. in the overhead, cut 2 was taken by vacuum distilling for 30 minutes at 100° to 105° C. and 8 mm Hg pressure. Cut 2 yielded about 6.7 grams of distillate while maintaining the overhead temperature at about 65° to 68° C. The residue after taking cut 2 was about 0.8 grams.

X-Ray diffraction analysis of the filter cake after calcining 30 minutes at 600° to 650° C. under helium showed $AlF_3$ (major) and $AlF_{1.96}OH_{1.04}$ (minor). Cut 2 and the residue was analyzed by gas chromatography/mass spectral (GC/MS) analysis and yielded about 78% diphenylsilane, about 20% toluene, and about 0.3% triethylamine. Hence about 68% diphenyldifluorosilane was converted to diphenylsilane ($Ph_2SiH_2$) with about 78% purity.

Similar procedures can be used to prepare monohydrocarbyl silanes and trihydrocarbyl silanes. Suitability of amine alanes and the like in reducing an organosilicon halide to the corresponding organosilicon hydride can be determined by a few simple tests as disclosed herein. It will be recognized and appreciated that reactants and conditions used in the process of this invention are susceptible to considerable variation. It is possible to vary many aspects of the above described invention without departing from the true spirit and scope thereof.

I claim:

1. A process for reducing an organosilicon halide to an organosilicon hydride comprising reacting an amine alane with the organosilicon halide such that the organosilicon hydride is formed.

2. The process of claim 1 wherein the organosilicon halide is represented by the general formula $$(R)_p SiX_{4-p}$$

wherein each R is independently, (1) a hydrocarbyl group such as alkyl, cycloalkyl, aryl, aralkyl, alkenyl, or alkynyl, containing up to 24 carbon atoms; (2) a halogenated hydrocarbyl group such as haloalkyl, halocycloalkyl, haloaryl, haloaralkyl, haloalkenyl, or haloalkynyl, or (3) a combination of (1) and (2); X is bromine, chlorine, fluorine, or iodine; and p is an integer from 1 to 3.

3. The process of claim 1 wherein the organosilicon halide is a bis-organosilicon halide represented by the general formula $$X_{3-p}R'_p Si-(R)-SiR'_p X_{3-p}$$

wherein each R radical is an alkyl, cycloalkyl, or aryl group containing 2 to 24 carbon atoms, R' is a hydrocarbyl group such as alkyl, cycloalkyl, aryl, or aralkyl, containing 1 to 24 carbon atoms; X is bromine, chlorine, fluorine, or iodine; and p is an integer from 0 to 2.

4. The process of claim 1 wherein the amine alane is a tertiary amine alane.

5. The process of claim 4 wherein the tertiary amine alane is a trialkylamine alane in which each alkyl group contains up to 12 carbon atoms.

6. The process of claim 5 wherein the trialkylamine alane is a triloweralkylamine alane selected from the group consisting of trimethylamine alane, triethylamine alane, N,N-dimethylethylamine alane, tripropylamine alane and tributylamine alane.

7. The process of claim 1 wherein n-hexylmethyldichlorosilane is reduced to n-hexylmethylsilane by reaction with triethylamine alane.

8. The process of claim 1 wherein diphenyldifluorosilane is reduced to diphenylsilane by reaction with triethylamine alane.

9. The process of claim 1 wherein the reaction is conducted in a liquid aromatic hydrocarbon medium.

10. The process of claim 9 wherein the liquid aromatic hydrocarbon medium is benzene, toluene, o-xylene, m-xylene, p-xylene, or ethylbenzene.

11. The process of claim 1 wherein the reaction is initiated at about room temperature.

12. A process for reducing an organosilicon halide to an organosilicon hydride comprising reacting an amine alane with the organosilicon halide in a liquid aromatic hydrocarbon medium.

13. The process of claim 12 wherein the amine alane is trimethylamine alane, triethylamine alane, N,N-dimethylethylamine alane, tripropylamine alane, or tributylamine alane.

14. The process of claim 12 wherein the liquid aromatic hydrocarbon medium is benzene, toluene, o-xylene, m-xylene, p-xylene, or ethylbenzene.

15. The process of claim 12 wherein the reaction is initiated at about room temperature.

16. A process for reducing an organosilicon halide to an organosilicon hydride comprising reacting an amine alane with the organosilicon halide in a liquid aromatic hydrocarbon medium wherein the organosilicon hydride is separated from the liquid aromatic hydrocarbon medium by distillation.

17. The process of claim 16 wherein the liquid aromatic hydrocarbon medium is benzene, toluene, o-xylene, m-xylene, p-xylene, or ethylbenzene.

18. The process of claim 16 wherein the reaction is initiated at about room temperature.

19. The process of claim 16 wherein the amine alane is trimethylamine alane, triethylamine alane, N,N-dimethylethylamine alane, tripropylamine alane, or tributylamine alane.

* * * * *